United States Patent [19]
Ha et al.

[11] Patent Number: 5,817,297
[45] Date of Patent: Oct. 6, 1998

[54] COMPOSITION FOR ENHANCING ORAL HYGIENE

[75] Inventors: Jae Mong Ha; Moon Moo Kim, both of Youseong-ku; Jong Heon Choi, Dong-ku; Hyeong Jun Lim, Youseong-ku; Sug Youn Chang, Youseong-ku; Ho Jeong Ahn, Youseong-ku; Eu Jene Choi, Songpa-ku; Seung Joon Lee, Seo-ku; Hong Soon Bak, Youseong-ku, all of Rep. of Korea

[73] Assignee: LG Chemical Ltd., Seoul, Rep. of Korea

[21] Appl. No.: 790,892

[22] Filed: Jan. 29, 1997

[30] Foreign Application Priority Data

Jul. 25, 1996 [KR] Rep. of Korea ...................... 96-30337
Jul. 25, 1996 [KR] Rep. of Korea ...................... 96-30499

[51] Int. Cl.⁶ ............................... A61K 7/16; A61K 7/18; A61K 7/26
[52] U.S. Cl. ................................. 424/58; 424/49; 424/52
[58] Field of Search ......................... 424/49–58

[56] References Cited

U.S. PATENT DOCUMENTS

| | | | |
|---|---|---|---|
| 4,115,313 | 9/1978 | Lyon et al. | 426/57 |
| 4,175,124 | 11/1979 | Hyldon et al. | 514/54 |
| 4,565,810 | 1/1986 | Castagnola et al. | 514/182 |
| 4,565,811 | 1/1986 | Di Schiena | 514/182 |
| 4,572,832 | 2/1986 | Kigasawa et al. | 514/772.1 |
| 4,866,044 | 9/1989 | Sato et al. | 514/77 |
| 5,180,573 | 1/1993 | Ha et al. | 424/49 |
| 5,260,462 | 11/1993 | Parenti | 552/550 |
| 5,321,019 | 6/1994 | Guiliani et al. | 524/169 |
| 5,487,902 | 1/1996 | Andersen et al. | 426/3 |
| 5,635,469 | 6/1997 | Fowler et al. | 510/406 |
| 5,651,997 | 7/1997 | Makino et al. | 424/682 |
| 5,681,606 | 10/1997 | Hutchinson et al. | 426/590 |

OTHER PUBLICATIONS

"The Reducing Effects on Dental Plaque Formation and Gingivitis of Toothpastes Containing Bamboo Salt and Several Herb Medicines" (in Korean), by Min, Byong–Son, et al., *The Journal of the Korean Dental Association*, vol. 34, No. 1, pp. 63–71 (Jan. 30, 1996).

"The Reducing Effects on Dental Plaque Formation, Gingivitis and Calculus Accumulation of Toothpaste Containing Bamboo Salt and Several Herb Medicines" (in Korean), by Kim, Min–Young, et al., *The Journal of the Korean Dental Association*, vol. 34, No. 6, pp. 433–442 (Jun. 30, 1996).

*Primary Examiner*—Shep K. Rose
*Attorney, Agent, or Firm*—Birch, Stewart, Kolasch & Birch LLP

[57] ABSTRACT

The present invention relates to a composition for enhancing oral hygiene which can effectively prevent and treat periodontal diseases and dental caries, characterized in that it contains as an effective component one or more component selected from ursodesoxycholic acid and chenodesoxycholic acid having a good inhibiting effect on collagenase, which is known as the inducer of gingivitis.

16 Claims, No Drawings

COMPOSITION FOR ENHANCING ORAL HYGIENE

BACKGROUND OF THE INVENTION

1. Field of the invention

The present invention relates to a composition for enhancing oral hygiene which is effective for the prevention and treatment of periodontal diseases and for the prevention of dental caries. More specifically, the present invention relates to a composition for enhancing oral hygiene which can effectively prevent and treat periodontal diseases and dental caries, characterized in that it contains one or more component selected from ursodesoxycholic acid and chenodesoxycholic acid having a good inhibiting effect on collagenase activity, as an effective component.

2. Background Art

Various oral diseases occurring in the oral tissues are caused by plaque formed by the action of numerous microorganisms present in oral cavity. Their importance in clinical and pathological view has been widely studied and also identified by many reseachers including Alexander (Alexander A. G., J. Periodent, 42, 21–28, 1971), Ash(Ash, M. M., J. Periodontol, 35, 424, 1964), etc.

Saliva is a unique mixture comprising electrolytes and other constituents, which play an important role in maintenance of oral health and digestion. The saliva contains various enzymes of which some enzymes including metalloproteinase show an enhanced enzymatic activity in patients suffering from periodontal diseases. Therefore, saliva enzymes are the important subject of study in view of prevention and treatment of periodontal diseases. Generally, it has been known that salivary gland, serum, leukocytes, epithelial cells, oral microorganisms, etc. are involved in production of such saliva enzymes.

Collagenase, which is one of metalloproteinase, plays a siginificant role in decomposition of connective tissues and is present in an inactivated form in the healthy oral cavity whereas in an activated form in the oral cavity of patients suffering from periodontal diseases. Therefore, considering that the inactivation of collagenase may significantly contribute to the treatment of periodontal diseases, it has been required to develop the substances having an effect of inhibiting collagenase.

As is well known, fel tauri (gall-bladder of Bos taurus demesticus Gmelin) and fel ursi (gall-bladder of Selenarctos thibetanus G. Cuvier) are the crude drugs originated from medicinal animals and have been widely known as having analgesic, cholagogic, sedative, spasmolytic and antiinflammatory effect, effect of treating chronic hepatitis, thoractic tumor, etc. In addition, Korean Laid-open Patent Publication Nos. 93-11992 and 93-11993 disclose that the oral hygienic agent prepared by mixing fel tauri salt, which is produced by mixing bovine bile juice with salt and heating the mixture at high temperature, bovine bile juice containing glycocholic acid, taurocholic acid, etc., and salt and then heating the mixture has an effect of inhibiting plaque formation and of preventing and treating periodontal diseases. However, fel tauri and fel ursi as the crude drug originated from medicinal animals has some problems that since they contains too numerous components, their stability is poor when they are applied to the medicinal product, it is possible to degenerate the crude materials themselves depending on the condition of storage and it is difficult to maintain the uniform medicinal effect.

Thus, the present inventors have studied to improve the above mentioned problems involved in the prior art and to develop an agent capable of fundamentally removing the cause of periodontal diseases to prevent the attack of periodontal diseases. As a result, we have identified that a composition containing one or more component selected from the group consisting of ursodesoxycholic acid and chenodes-oxycholic acid which are the main components of fel ursi, as the effective component can effectively inhibit the activity of collagenase as the causal substance of periodontal diseases, and has an improved storage stability and safety to human subject in comparison to the composition containing fel tauri or fel ursi itself, and thus completed the present invention.

Accordingly, the object of the present invention is to provide to a composition for enhancing oral hygiene which comprises one or more component selected from the group consisting of ursodesoxycholic acid and chenodesoxycholic acid as an effective component.

In addition, another object of the present invention is to provide a composition for enhancing oral hygiene which comprises one or more component selected from the group consisting of ursodesoxycholic acid and chenodesoxycholic acid as an effective component and further contains triclosan to provide a superior inhibiting effect on plaque formation.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

The present invention relates to a composition for enhancing oral hygiene whcih comprises as an effective component one or more component selected from the group consisting of ursodesoxycholic acid and chenodesoxycholic acid.

In the composition of the present invention, ursodesoxycholic acid and chenodesoxycholic acid as the effective components can be used individually or in the form of a mixture. Since ursodesoxycholic acid and chenodesoxycholic acid can be correspondingly substituted with each other, when the mixture of ursodesoxycholic acid and chenodes-oxycholic acid is used in the composition of the present ivnention, the mixing ratio of said two components is not critically limited. Generally, ursodesoxycholic acid and chenodesoxycholic acid are mixed in the ratio of 100:1 to 1:100 on the basis of weight.

In the composition of the present invention, ursodesoxycholic acid and chenodesoxycholic acid, individually or as the mixture, are contained in the ratio of 0.02 to 1.0 wt %, preferably 0.02 to 0.6 wt %, with respect to the total weight of the composition. When the mixture of ursodesoxycholic acid and chenodesoxycholic acid is used, the mixture can be used in the same amount as any one component singly used to provide the substantially comparable effect to that obtained from one component. If the amount of the effective component is lower than 0.02 wt %, the effect of preventing gingivitis of the composition is too weak to establish the desired purpose, and if the amount of the effective component is in excess of 1.00 wt %, it is not preferable since an increase of the desired medicinal effect in proportion to an increase in the content of the effective component cannot be obtained.

If desired, the composition of the present invention can additionally include triclosan which has a good bactericidal effect and also an effect of removing plaque and of preventing and treating periodontal diseases, to provide an increased effect of inhibiting plaque formation and alleviating gingivitis. When triclosan is included in the present composition, the composition contains 0.01 to 1.0 wt %, preferably 0.02 to 0.6 wt % of ursodesoxycholic acid or chenodesoxycholic acid or the mixture thereof and 0.0001 wt % to 1.0 wt %, particularly 0.001 to 0.300 wt % of triclosan, with respect to the total weight of the composition. If triclosan is added in an amount of lower than 0.0001 wt %, the desired synergistic effect is weak, and if the amount of triclosan is in excess of 1.000 wt %, it is not preferable since the synergistic effect due to the addition of triclosan cannot be obtained.

The composition of the present invention additionally contains, if necessary, one or more substance suitably selected from the group consisting of fluoride compounds such as sodium fluoride, sodium fluorophosphate, fluoroamine, tin fluoride, etc., bamboo salt, chlorhexidine, tranexamic acid, allantoins, caproic acid, enzymes, and extracts of medicinal herbs such as *Phellodendri cortex, Platycodi radix, Schizonepetae herba, Gardeniae fructus, Glycyrrhizae radix, Sanguinaria radix,* etc. as the adjuvant effective component, depending on the kind of the composition to be prepared. Particularly, it is preferable to combine bas the adjuvant effective component bamboo salt, extract of *Phellodendri cortex,* extract of *Platycodi radix,* extract of *Schizonepetea herba* and fluoride compound in a certain ratio. In this case, with respect to the total weight of the composition, bamboo salt may be used in the ratio of 1.0 to 5.0 wt %, the total weight of the extracts of three medicinal herbs may be in the range of 0.01 to 5.0 wt %, and fluoride compound may be used in a suitable amount conventionally used in this technical field, specifically in the ratio of 0.1 to 1.0 wt %. If the adjuvant effective components are used in an amount lower than the preferable amount, it is difficult to obtain the desired effect, and if the adjuvant effective components are used in excess of the preferable amount, the condition of the final product, for example, dentifrice is poor.

The composition for enhancing oral hygiene according to the present invention can be prepared in the form of dentifrice, oral rinse, chewing gum, oral massage cream, etc., by using conventional additives including polishing agent, wetting agent, binding agent, foaming agent, sweetening agent, preservative, medicinal components, perfumes, acidity regulating agent, whitening agent, etc. depending on the purpose of use.

When the composition of the present invention is prepared in the form of dentifrice, the dentifrice composition includes additives conventionally used for preparation of dentifrice, for example, polishing agent, wetting agent, binding agent, foaming agent, sweetening agent, perfumes, acidict regulating agent, whitening agent, etc. are included in addition to the above-mentioned effective components.

In this case, as the polishing agent one or more substance selected from the group consisting of calcium monohydrogenphosphate, precipitated silica, calcium carbonate, hydrated alumina, kaolin and sodium hydrogen carbonate(NaHCO$_3$) is used in an amount of 20 to 60 wt % with respect to the total weight of the composition.

As the wetting agent, one or more substance selected from the group consisting of glycerin, sorbitol, non-crystalline sorbitol solution, propylene glycol, polyethylene glycol and xylitol is used in an amount of 20 to 60 wt % with respect to the total weight of the composition. Preferably, the mixture of glycerin or non-crystalline sorbitol solution and propylene glycol or polyethylene glycol which are combined in the ratio of 10:1 to 1:1 on the basis of weight is used in an amount of 20 to 50 wt % with respect to the total weight of the composition.

As the binding agent, one or more substance selected from the group consisting of carrageenan, xanthan gum, sodium carboxymethylcellulose, carboxyvinyl polymer, sodium alginate, bee gum and laponite is used in an amount of 0.1 to 3.0 wt %, preferably 0.5 to 2.0 wt %, with respect to the total weight of the composition.

As the foaming agent, one or more substance selected from the group consisting of anionic surfactant such as sodium laurylsulfate, sodium laurylsarcosinate, etc. and sorbitan fatty acid ester, polyoxyethylene hydrogenated castor oil and polyoxyethylene-polyoxypropylene condensed polymers can be used in an amount of 0.5 to 5.0 wt %, preferably 0.5 to 3.5 wt %, with respect to the total weight of the composition.

In addition, with respect to the total weight of the composition, one or more substance selected from saccharin sodium, aspartam and glycyrrhizic acid is used in an amount of 0.05 to 0.5 wt % as the sweetening agent; and one or more selected from para-oxybenzoic acid ester and sodium benzoate is used as the preservative.

As the perfume peppermint oil, spearmint oil, menthol, carbon, etc. are mixed in a suitable ratio. Preferably, anise oil may be added in a suitable amount to the mixture of the above mentioned perfumes combined in a certain mixing ratio. As the acidity regulating agent, one or more substance selected from the group consisting of phosphoric acid, sodium phosphate, citric acid, sodium citrate, succinic acid, sodium succinate, tartaric acid and sodium tartrate is used to adjust the pH value within the range of 5 to 8. In addition, titanium oxide is used in an amount of 0.1 to 2.0 wt %, with respect to the total weight of the composition, as the whitening agent.

When the composition according to the present ivnention is prepared in the form of an oral rinse, it is prepared in the following method.

The oral rinse composition is generally composed of the alcoholic part and the purified water part. Therefore, each component is dissolved in the part in which it is well dissolved, and then the resulting two parts are mixed to prepare the oral rinse composition. In this case, ethanol is used to provide a refreshing feeling in using the oral rinse and to dissolve the slightly water-soluble perfume and preservative. Although the emission of perfume is increased in proportion to the content of ethanol, ethanol is generally used in an amount of 1.0 to 30.0 wt %, preferably 2.0 to 20 wt %, with respect to the total weight of the composition since the excessive amount of ethanol provides a bitter taste and stimulates the oral mucous membrane.

The components essentially used in preparing the oral rinse composition can include solubilizing agent, wetting agent, perfume, sweetening agent, preservative, etc., in addition to medicinal components such as bactericidal agent, enzyme, anti-plasminic agent, etc.

The bactericical agent which can be used includes antibiotics, cationic surfactant and quaternary ammonium compound. However, since antibiotics may induce hypersensitivity and resistance of miroorganisms, it should be used under careful prior examination. As the enzyme, one or more selected from dextranase as the main constituent of plaque, glucoamylase which can decompose starch present in food residue and other adhesive polysaccharide substances present in oral cavity, alpha-amylase, beta-amylase, glucose oxidase which can oxidize glucose, which causes dental caries by the mechanism that glucose is anaerobically decomposed by microorganisms present in oral cavity to produce organic acid which decays the surface of teeth, to produce hydrogen peroxide, and lysozyme which disrupts the cell wall by the direct action thereon to provide bactericidal activity can be used in an amount of 0.1 to 100,000 units per gram of the composition. The anti-plasminic agent is used for the purpose of inhibition of gingival inflammation and bleeding to prevent periodontal diseases. For this purpose, one or more selected from tranexamic acid, aminocaproic acid, etc. is used in an amount of 0.05 to 0.30 wt % with respect to the total weight of the composition.

As the solubilizing agent for solubilizing perfume in water, one or more substance selected from the group consisting of anionic surfactant such as sodium laurylsulfate, sodium laurylsarcosinate, etc., sorbitan fatty acid ester, polyoxyethylene hydrogenated castor oil, polyoxyethylene-polyoxypropylene condensed polymers, higher alkyl acetates and polyoxyethylene derivatives of sorbitan fatty acid ester, preferably one or more substance selected from the group consisting of sodium laurylsulfate, polyoxyethylene hydrogenated castor oil and polyoxyethylene-polyoxypropylene condensed polymers is used in an amount of 0.1 to 3.0 wt %, preferably 0.5 to 3.0 wt %, with respect to the total weight of the composition.

To provide the stability, sweet taste and some viscosity of the product the wetting agent is used. As the example of wetting agent which can be used for this purpose, glycerin, sorbitol solution, non-crystalline sorbitol solution, propylene glycol, polyethylene glycol and xylitol can be mentioned, with glycerin, non-crystalline sorbitol solution and xylitol being preferable. The wetting agent is used generally in an amount of 2.0 to 40.0 wt %, preferably in an amount of 3.0 to 20.0 wt %, with respect to the total weight of the composition.

In addition, to improve the feeling-in-use perfume and sweetening agent can be used. As the perfume, peppermint, spearmint, L-menthol, eucalyptus or methylsalicylate is used in an amount of 0.1 to 1.0 wt %; and lactose, sorbitol, aspartam, saccharin sodium, etc. can be used as the sweetening agent. Particularly, saccharin sodium is used generally in an amount of 0.001 to 0.1 wt % with respect to the total weight of the composition.

As the preservative, one or more substance selected from benzoic acid, sodium benzoate, para-oxybenzoic acid ester, cresol and formalin is used in an amount of 0.05 to 0.15 wt % with respect to the total weight of the composition. Preferably, benzoic acid, sodium benzoate, paraoxybenzoic acid methyl or propyl ester can be used as the preservative.

In addition, the oral rinse composition of the present invention can further include buffering agent, coloring agent, sodium chloride, etc. Among them, the buffering agent for adjusting the acidity of the oral rinse composition is one or more substance seleccted from sodium dihydrogenphosphate, disodium hydrogenphosphate, sodium phosphate, citric acid, sodium citrate, succinic acid, sodium succinate, tartaric acid and sodium tartrate. Preferably, one or more selected from sodium dihydrogenphosphate and sodium phosphate can be used. The coloring agent is used to increase the value of commercial product and to fit with the purpose of use of the oral rinse composition. For this, any suitable edible coloring agents can be used. Sodium chloride is used generally for the purpose of alleviation of gingival inflammation and bactericidal activity, in an amount of 3 to 35 wt % with respect to the total weight of the composition.

The present invention will be more specifically illustrated by the following examples and experiments. However, it should be noted that these examples intend to help the clear understanding of the present invention and the technical scope of the present invention is not limited to these examples in any manner.

EXAMPLES 1 TO 6 AND COMPARATIVE EXAMPLES 1 TO 4

The dentifrice compositions of Examples 1 to 6 according to the present invention and the dentifrice compositions of Comparative Examples 1 to 4 were prepared according to the constitutional ratio described in the following Table 1. Specifically, the powdery components including sodium carboxymethylcellulose, saccharin sodium, para-oxybenzoic acid ester, etc. were dispersed in sorbitol solution and glycerin as the wetting components and the resulting dispersion was diluted with purified water and primary blended in the mixer. To this mixture was added polishing agent and medicinal components. Finally, sodium alkylsulfate as the foaming agent, stabilizers and perfumes were added thereto and mixed under vacuum to prepare the desired dentifrice composition.

TABLE 1

| Components | Ex. 1 | Ex. 2 | Ex. 3 | Ex. 4 | Ex. 5 | Ex. 6 | Comp. Ex. 1 | Comp. Ex. 2 | Comp. Ex. 3 | Comp. Ex. 4 |
|---|---|---|---|---|---|---|---|---|---|---|
| calcium monohydrogen phosphate | 40.00 | 40.00 | 20.00 | — | — | 40.00 | 40.00 | 40.00 | 40.00 | — |
| calcium carbonate | — | — | 20.00 | — | 38.00 | — | — | — | — | 38.00 |
| precipitated silica | — | — | — | 20.00 | — | — | — | — | — | — |
| sorbitol | 25.00 | 25.00 | 25.00 | 40.00 | 25.00 | — | 30.00 | 30.00 | — | — |
| glycerin | — | — | — | — | — | 25.00 | — | — | 25.00 | 25.00 |
| sodium lauryl sulfate | 1.50 | 1.50 | 1.50 | 1.50 | 1.50 | 1.50 | 1.50 | 1.50 | 1.50 | 1.50 |
| saccharin sodium | 0.10 | 0.10 | 0.10 | 0.10 | 0.10 | 0.10 | 0.10 | 0.10 | 0.10 | 0.10 |
| para-oxybenzoic acid ester | 0.10 | 0.10 | 0.10 | 0.10 | 0.10 | 0.10 | 0.10 | 0.10 | 0.10 | 0.10 |
| sodium carboxymethylcellulose | 1.00 | 1.00 | 1.00 | 1.00 | 1.00 | — | 1.00 | 1.00 | — | 1.00 |
| carrageenan | — | — | — | — | — | 0.90 | — | — | 0.90 | — |

TABLE 1-continued

| Components | Ex. 1 | Ex. 2 | Ex. 3 | Ex. 4 | Ex. 5 | Ex. 6 | Comp. Ex. 1 | Comp. Ex. 2 | Comp. Ex. 3 | Comp. Ex. 4 |
|---|---|---|---|---|---|---|---|---|---|---|
| ursodesoxycholic acid | 0.02 | 0.20 | 0.60 | 1.00 | 0.10 | 0.02 | 0.01 | 2.00 | — | — |
| chenodesoxycholic acid | — | — | — | — | 0.10 | — | — | — | — | — |
| bamboo salt | — | — | — | — | — | 3.00 | — | — | 3.00 | — |
| disodium fluorophosphate | 0.76 | 0.76 | 0.76 | 0.76 | 0.76 | 0.76 | 0.76 | 0.76 | 0.76 | — |
| extract of Phellodendri cortex | — | — | — | — | — | 0.10 | — | — | 0.10 | — |
| extract of Platycodi radix | — | — | — | — | — | 0.10 | — | — | 0.10 | — |
| extract of Schizonepetae herba | — | — | — | — | — | 0.10 | — | — | 0.10 | — |
| Purified water added to | 100.0 | 100.0 | 100.0 | 100.0 | 100.0 | 100.0 | 100.0 | 100.0 | 100.0 | 100.0 |

Note: unit = % by weight (wt %)

EXAMPLES 7 TO 12 AND COMPARATIVE EXAMPLES 5 TO 8

The oral rinse compositions of Examples 7 to 12 according to the present invention and the oral rinse compositions of Comparative Examples 5 to 8 were prepared according to the constitutional ratio described in the following Table 2 by means of a conventional method. Specifically, components which are soluble in ethanol were completely dissolved in ethanol solvent and then perfume was added thereto. The mixture was thoroughly stirred and then added to the purified water part as previously prepared (solution prepared by dissolving wetting agent and other components in purified water) with stirring to obtain the intimate solution. Then, the resulting solution was filtered to produce the desired oral rinse composition.

TABLE 2

| Components | Ex. 7 | Ex. 8 | Ex. 9 | Ex. 10 | Ex. 11 | Ex. 12 | Comp. Ex. 5 | Comp. Ex. 6 | Comp. Ex. 7 | Comp. Ex. 8 |
|---|---|---|---|---|---|---|---|---|---|---|
| ethanol(90%) | 10.00 | 10.00 | 10.00 | — | — | 10.00 | 10.00 | 10.00 | 10.00 | — |
| glycerin | 10.00 | — | 10.00 | — | — | — | — | — | — | 38.00 |
| sorbitol solution | — | 15.00 | — | 15.00 | — | — | — | — | — | — |
| xylitol | — | — | — | — | 10.00 | 10.00 | — | — | — | — |
| sodium lauryl sulfate | 1.20 | 1.20 | 1.20 | 1.20 | — | 1.20 | 1.20 | 1.20 | — | — |
| polyoxyethylene-polyoxypropylene copolymer (Poloxamer 407) | — | — | — | — | 1.20 | — | — | — | 1.20 | — |
| saccharin sodium | 0.50 | 0.50 | 0.50 | 0.50 | 0.50 | 0.50 | 0.50 | 0.50 | 0.50 | 0.50 |
| para-oxybenzoic acid ester | 0.10 | 0.10 | 0.10 | 0.10 | 0.10 | 0.10 | 0.10 | 0.10 | 0.10 | 0.10 |
| ursodesoxycholic acid | 0.02 | 0.20 | 0.60 | 1.00 | 0.10 | 0.02 | 0.01 | 2.00 | — | — |
| chenodesoxycholic acid | — | — | — | — | 0.10 | — | — | — | — | — |
| bamboo salt | — | — | — | — | — | 3.00 | — | — | 3.00 | — |
| disodium fluorophosphate | 0.76 | 0.76 | 0.76 | 0.76 | 0.76 | 0.76 | 0.76 | 0.76 | 0.76 | — |
| extract of Phellodendri cortex | — | — | — | — | — | 0.10 | — | — | 0.10 | — |
| extract of Platycodi radix | — | — | — | — | — | 0.10 | — | — | 0.10 | — |
| extract of Schizonepetae herba | — | — | — | — | — | 0.10 | — | — | 0.10 | — |
| perfume | 1.00 | 1.00 | 1.00 | 1.00 | 1.00 | 1.00 | 1.00 | 1.00 | 1.00 | 1.00 |
| Purified water added to | 100.0 | 100.0 | 100.0 | 100.0 | 100.0 | 100.0 | 100.0 | 100.0 | 100.0 | 100.0 |

Note: unit = % by weight (wt %)

EXAMPLES 13 TO 19 AND COMPARATIVE EXAMPLES 9 TO 11

The dentifrice compositions of Examples 13 to 19 according to the present invention and the dentifrice compositions of Comparative Examples 9 to 11 were prepared according to the constitutional ratio described in the following Table 3.

Specifically, the powdery components including sodium carboxymethylcellulose, saccharin sodium, para-oxybenzoic acid ester as the preservative, etc. were dispersed in sorbitol solution and glycerin as the wetting components and the resulting dispersion was diluted with purified water and primary blended in the mixer. To this mixture was added polishing agent and medicinal components. Finally, sodium alkylsulfate as the foaming agent, stabilizers and perfumes were added thereto and mixed under vacuum to prepare the desired dentifrice composition.

Both the chewing gum composition of Example 20 and the oral massage cream composition of Example 21 as above showed a good effect of alleviating gingivitis.

Experiment 1

The inhibition effects on collagenase activity of various substances including ursodesoxycholic acid and chenodesoxycholic acid as the effective components of the composition for enhancing oral hygiene according to the present invention were determined and compared according to the following method.

TABLE 3

| Components | Ex. 13 | Ex. 14 | Ex. 15 | Ex. 16 | Ex. 17 | Ex. 18 | Ex. 19 | Comp. Ex. 9 | Comp. Ex. 10 | Comp. Ex. 11 |
|---|---|---|---|---|---|---|---|---|---|---|
| calcium monohydrogen phosphate | 40.00 | 40.00 | 20.00 | — | — | 40.00 | 40.00 | 40.00 | 40.00 | — |
| calcium carbonate | — | — | 20.00 | — | 38.00 | — | — | — | — | 38.00 |
| precipitated silica | — | — | — | 20.00 | — | — | — | — | — | — |
| sorbitol | 25.00 | 25.00 | 25.00 | 40.00 | 25.00 | — | 30.00 | 30.00 | — | — |
| glycerin | — | — | — | — | — | 25.00 | — | — | 25.00 | 25.00 |
| sodium lauryl sulfate | 1.50 | 1.50 | 1.50 | 1.50 | 1.50 | 1.50 | 1.50 | 1.50 | 1.50 | 1.50 |
| saccharin sodium | 0.10 | 0.10 | 0.10 | 0.10 | 0.10 | 0.10 | 0.10 | 0.10 | 0.10 | 0.10 |
| para-oxybenzoic acid ester | 0.10 | 0.10 | 0.10 | 0.10 | 0.10 | 0.10 | 0.10 | 0.10 | 0.10 | 0.10 |
| sodium carboxy-methylcellulose | 1.00 | 1.00 | 1.00 | 1.00 | 1.00 | — | 1.00 | 1.00 | 1.00 | 1.00 |
| carrageenan | — | — | — | — | — | 0.90 | — | — | 0.90 | — |
| ursodesoxycholic acid | 0.01 | 0.02 | 0.02 | 0.20 | 0.20 | 0.01 | 0.10 | 0.001 | — | 1.50 |
| chenodesoxycholic acid | — | — | — | — | — | 0.01 | — | — | — | — |
| triclosan | 0.0001 | 0.0001 | 0.0100 | 0.1000 | 0.3000 | 0.0001 | 1.0000 | 0.0001 | 0.0300 | 1.5000 |
| disodium fluorophosphate | 0.76 | 0.76 | 0.76 | 0.76 | 0.76 | 0.76 | 0.76 | 0.76 | 0.76 | 0.76 |
| Purified water added to | 100.0 | 100.0 | 100.0 | 100.0 | 100.0 | 100.0 | 100.0 | 100.0 | 100.0 | 100.0 |

Note: unit = % by weight (wt %)

EXAMPLE 20

Chewing Gum

| | |
|---|---|
| gum base | 25.00% |
| sorbitol | 44.00% |
| manitol | 12.00% |
| glycerin | 13.00% |
| lecithin | 0.50% |
| aspartam | 2.00% |
| ursodesoxycholic acid | 0.02% |
| perfume | 1.00% |

EXAMPLE 21

Oral Massage Cream (Ointment)

| | |
|---|---|
| monolauryl glycerin | 3.00% |
| oleic alcohol | 5.00% |
| polyethylene glycol | 15.00% |
| white vaseline | 3.00% |
| monosodium N-palmitic glutamic acid | 0.50% |
| hydroxyethylcellulose | 5.00% |
| tocopherol acetate | 0.10% |
| ursodesoxycholic acid | 0.20% |
| aspartam | 0.20% |
| perfume | 0.30% |
| purified water added to | 100.0% |

1) Test substances ursodesoxycholic aicd, chenodesoxycholic acid, fel tauri salt, bamboo salt, common salt, *Machili cortex, Phellodendri cortex, Platycodi radix, Schizonepetae herba, Glycyrrhizae radix, Angelicae gigantis radix, Chamomillae flos,* Myrrha, *Theae folium, Taraxaci radix* cum Herba, *Lonicerae flos, Ciniicifugae rhizoma.*

2) Test method

① 100 μl of 2% azocol solution was added to the test tube and then 190 μl of buffer solution (0.05M Tris-HCl, 1 mM $CaCl_2$, pH 7.8) was added thereto.

② To the resulting solution as prepared above was added to each test substance in the following concentration:

Ursodesoxycholic acid (10% ethanol solution) or chenodesoxycholic acid (10% ethanol solution) was added to the final concentration of 0.02%;

Fel tauri salt, bamboo salt or common salt was dissolved in the buffer solution as mentioned above and then added to the final concentration of 2.0%;

*Machili cortex, Phellodendri cortex, Platycodi radix, Schizonepetae* herba, *Glycyrrhizae radix, Angelicae gigantis radix, Chamomillae flos, Myrrha, Theae folium, Taraxaci radix* cum Herba, *Lonicerae flos* or *Cimicifugae rhizoma* was added in the form of 30% ethanol extract to the final concentration of 0.1%.

③ 100 μl of collagenase having 100 ppm concentration was added and then the mixture was maintained in a 37° C. incubator for 18 hours. (Separately, the standard activity curve was prepared from 10, 100, 200 μl of collagenase.)

④ The test tubes were centrifuged for 5 minutes.

⑤ The supernatant was separated from the test tube and then added to the cell. The absorbance at 540 nm was measured by spectrophotometer and then the activity of the test group was determined from the standard activity curve.

3) Result

TABLE 4

Inhibition effect of test substance on collagenase activity

| Items | Absorbance (540 nm) | Enzyme activity inhibition (%) | Remarks |
| --- | --- | --- | --- |
| Blank test | 0.003 | | exclusion of collagenase |
| Control group | 0.323 | 0.00 | containing collagenase |
| Ursodesoxycholic acid | 0.243 | 45.64 | |
| Chenodesoxycholic acid | 0.260 | 39.23 | |
| Fel tauri salt | 0.330 | −6.15 | |
| Babmboo salt | 0.320 | 1.98 | |
| Common salt | 0.330 | −6.15 | |
| Extract of Machili cortex | 0.298 | 17.74 | containing collagensae, 30% alcohol extract |
| Extract of Phellodendri cortex | 0.315 | 5.80 | |
| Extract of Platycodi radix | 0.325 | −2.01 | |
| Extract of Schizonepetae herba | 0.320 | 1.98 | |
| Extract of Glycyrrhizae radix | 0.325 | −2.01 | |
| Extract of Angelicae gigantis radix | 0.325 | −2.01 | |
| Extract of Chammomillae flos | 0.328 | −4.48 | |
| Extract of Myrrha | 0.310 | 9.48 | |
| Extract of Theae folium | 0.305 | 13.02 | |
| Extract of Taraxaci radix cum Herba | 0.300 | 1.98 | |
| Extract of Lonicerae flos | 0.328 | −4.48 | |
| Extract of Cimicifugae rhizoma | 0.330 | −6.15 | |

TABLE 5

Inhibition effect on collagenase activity of ursodesoxycholic aicd and chenodesoxycholic acid depending on their content and mixing ratio

| Content of ursodesoxycholic acid (%) | Content of chenodesoxycholic acid (%) | Absorbance (540 nm) | Enzyme activity inhibition (%) |
| --- | --- | --- | --- |
| 0.001 | — | 0.326 | −2.82 |
| 0.010 | — | 0.305 | 13.02 |
| 0.020 | — | 0.243 | 45.64 |
| 0.050 | — | 0.215 | 57.54 |
| 0.100 | — | 0.166 | 71.26 |
| 0.150 | — | 0.050 | 88.60 |
| 0.200 | — | 0.005 | 92.03 |
| 0.600 | — | 0.002 | 92.22 |
| 1.000 | — | 0.000 | 92.34 |
| 2.000 | — | 0.000 | 92.34 |
| — | 0.001 | 0.324 | −1.20 |
| — | 0.010 | 0.315 | 6.55 |
| — | 0.020 | 0.260 | 39.23 |
| — | 0.050 | 0.230 | 52.15 |
| — | 0.100 | 0.180 | 67.87 |
| — | 0.150 | 0.052 | 88.41 |
| — | 0.200 | 0.007 | 91.91 |
| — | 0.600 | 0.002 | 92.22 |
| — | 1.000 | 0.002 | 92.22 |
| — | 2.000 | 0.002 | 92.22 |
| 0.005 | 0.005 | 0.310 | 9.48 |
| 0.025 | 0.025 | 0.220 | 55.81 |
| 0.050 | 0.050 | 0.180 | 67.87 |
| 0.100 | 0.100 | 0.005 | 92.03 |
| 0.500 | 0.500 | 0.002 | 92.22 |

As can be seen from the above Tables 4 and 5, ursodesoxycholic acid and chenodesoxycholic acid show superior inhibition effect on collagenase activity in comparison with extracts of other medicinal herbs. Their effects begin at the concentration of 0.01% and reach the maximum level at the concentration of 0.6%. However, the effect is not significantly increased at the concentration in excess of 0.6%. In addition, when the mixture of ursodesoxycholic acid and chenodesoxycholic acid is used, the effect resulted from the total content of the mixture is similar to that resulted from the same content of each effective component.

Experiment 2

The inhibition effect of ursodesoxycholic acid, chenodesoxycholic acid and triclosan as the effective components of the composition for enhancing oral hygiene according to the present invention on plaque formation was determined and compared according to the following method.

1) Test substance

Ursodesoxycholic acid, Chenodesoxycholic aicd, Triclosan.

2) Test method

① Test strain, Streptococcus mutans 10449, type C was cultured in brain-heart infusion agar medium and then the cultured strain was inoculated on THB(Todd Hewitt Broth) and cultured at 37° C. for 15 hours.

② The small glass bar was sterilized and then weighed.

③ This glass bar was introduced into the test tube in which the medium containing sucrose is included. The test substance was added at a given concentration to the test tube and then the test microorganism strain was added thereto. The test tube was cultured at 37° C. for 24 hours.

④ After incubation, the glass bar was carefully removed from the test tube and dried at 37° C. for one day. The final weight of the glass bar was measured. The control group was treated in the same manner as the test group except that the test substance is not added.

⑤ From the measured result, the plaque formation percentage was calculated according to the following equation:

Plaque formation percentage (%) =

$$\frac{\text{Test Group (final weight-initial weight)}}{\text{Control Group (final weight-initial weight)}} \times 100$$

3) Results

TABLE 6

| | ursodes-oxycholic acid | chenodes-oxycholic acid | triclosan | plaque formation(%) | pH |
|---|---|---|---|---|---|
| 1 | 0.100 | — | — | 100.0 | 4.2 |
| 2 | — | 0.100 | — | 100.0 | 4.2 |
| 3 | — | — | 0.0010 | 100.0 | 4.3 |
| 4 | — | — | 0.0050 | 100.0 | 4.3 |
| 5 | — | — | 0.0100 | 100.0 | 4.3 |
| 6 | — | — | 0.0300 | 50.0 | 4.5 |
| 7 | — | — | 0.0500 | 0.0 | 7.5 |
| 8 | 0.002 | — | 0.0001 | 100.0 | 4.5 |
| 9 | 0.010 | — | 0.0001 | 80.0 | 5.2 |
| 10 | 0.020 | — | 0.0001 | 0.0 | 6.8 |
| 11 | — | 0.002 | 0.0001 | 100.0 | 4.5 |
| 12 | — | 0.010 | 0.001 | 80.0 | 5.1 |
| 13 | — | 0.020 | 0.0001 | 0.0 | 6.8 |
| 14 | 0.010 | 0.010 | 0.0001 | 0.0 | 6.8 |

As can be seen from the result described in the above Table 6, when ursodesoxycholic acid and/or chenodesoxycholic acid is mixed with triclosan in a certain ratio, the mixture shows a superior inhibiting effect on plaque formation.

Experiment 3

The effect of inhibiting plaque formation and gingivitis was tested using the dentifrice compositions of Examples 1 to 6 and Comparative Examples 1 to 4 described in Table 1 according to the following method. The results are described in the following Tables 7 and 8.

1) Test method

① The test subjects were selected and were given the explanation of oral medical examination.

② The test subjects were divided such that the group for each composition of examples and comparative examples includes 10 subjects, and then had the education of correct brushing method. The test subject were subjected to the oral medical examination to measure the plaque index (Quigley-Hein Index modified by Turesky) and the gingivitis index (Gingival Bleeding Index, Loe-Silness Index).

③ Before the test, all the test subjects were subjected to teeth scaling.

④ The placebo dentifrice(calcium monohydrogenphosphate 40%, glycerin 25%, sodium laurylsulfate 1.5%, sodium saccharin 0.1%, paraoxybenzoic acid ester 0.1%, sodium carboxymethylcellulose 1%, purified water added to 100%) was used for 2 weeks and then the oral medical exmamination was conducted again to measure the plaque index and the gingivitis index as the initial value.

⑤ The test subjects were allowed to brush using the dentifrice of examples and comparative examples for 4 weeks, three times for one day, according to the same method as usual. The oral medical examination was conducted at the second and fourth weeks to determine the plaque index score and the gingivitis index score.

⑥ The score obtained after 4 weeks was compared with the initial value and examined for the statistic significance using T-test.

TABLE 7

Plaque index score

| Test dentifrice | Initial index | Index after 2 weeks | Index after 4 weeks | Improvement index |
|---|---|---|---|---|
| Example 1 | 1.50 ± 0.32 | 1.30 ± 0.27 | 1.07 ± 0.34 | 0.43 ± 0.28 |
| Example 2 | 1.54 ± 0.21 | 1.30 ± 0.25 | 1.12 ± 0.20 | 0.42 ± 0.22 |
| Example 3 | 1.54 ± 0.19 | 1.27 ± 0.31 | 1.08 ± 0.28 | 0.46 ± 0.28 |
| Example 4 | 1.47 ± 0.32 | 1.24 ± 0.32 | 0.98 ± 0.30 | 0.49 ± 0.29 |
| Example 5 | 1.54 ± 0.35 | 1.17 ± 0.32 | 1.10 ± 0.26 | 0.44 ± 0.32 |
| Example 6 | 1.52 ± 0.26 | 1.08 ± 0.19 | 0.75 ± 0.10 | 0.77 ± 0.13 |
| Comp. Example 1 | 1.53 ± 0.28 | 1.23 ± 0.26 | 1.13 ± 0.32 | 0.40 ± 0.32 |
| Comp. Example 2 | 1.52 ± 0.31 | 1.19 ± 0.32 | 0.96 ± 0.17 | 0.48 ± 0.32 |
| Comp. Example 3 | 1.53 ± 0.26 | 1.10 ± 0.19 | 0.81 ± 0.10 | 0.72 ± 0.13 |
| Comp. Example 4 | 1.53 ± 0.32 | 1.37 ± 0.32 | 1.29 ± 0.28 | 0.24 ± 0.35 |

TABLE 8

Gingivitis index score

| Test dentifrice | Initial index | Index after 2 weeks | Index after 4 weeks | Improvement index |
|---|---|---|---|---|
| Example 1 | 1.21 ± 0.32 | 1.05 ± 0.38 | 0.86 ± 0.35 | 0.35 ± 0.18 |
| Example 2 | 1.23 ± 0.24 | 0.95 ± 0.27 | 0.76 ± 0.24 | 0.47 ± 0.17 |
| Example 3 | 1.23 ± 0.27 | 0.89 ± 0.19 | 0.63 ± 0.18 | 0.60 ± 0.17 |
| Example 4 | 1.22 ± 0.23 | 0.84 ± 0.16 | 0.57 ± 0.12 | 0.65 ± 0.12 |
| Example 5 | 1.24 ± 0.18 | 0.96 ± 0.30 | 0.78 ± 0.25 | 0.42 ± 0.23 |
| Example 6 | 1.19 ± 0.21 | 0.60 ± 0.20 | 0.34 ± 0.12 | 0.85 ± 0.09 |
| Comp. Example 1 | 1.23 ± 0.23 | 1.15 ± 0.19 | 1.01 ± 0.15 | 0.22 ± 0.32 |
| Comp. Example 2 | 1.18 ± 0.33 | 0.83 ± 0.21 | 0.55 ± 0.18 | 0.63 ± 0.32 |
| Comp. Example 3 | 1.20 ± 0.18 | 0.84 ± 0.19 | 0.48 ± 0.10 | 0.72 ± 0.13 |
| Comp. Example 4 | 1.19 ± 0.31⁻ | 1.12 ± 0.32 | 1.08 ± 0.48 | 0.11 ± 0.32 |

As can be seen from the above Table 7, as the result of the siginificance examination in the plaque index measured after using the dentifrices of Examples 1 to 6 and Comparative Examples 1 to 4 for 4 weeks, it has been identified tht the use of the compositions of Examples 1 to 6 and Comparative Examples 1 to 3 provides a siginificant inhibiting effect on plaque formation in comparison with before use of the composition. However, the effects of the compositions of Examples 1 to 5 and Comparative Examples 1 to 2 have no significant difference from each other and the effects of the compositions of Example 6 and Comparative Example 3 show a significant difference from that of the compositions of Examples 1 to 5 and Comparative Examples 1 to 2. In addition, the composition of Example 6 does not show any siginificant difference from that of Comparative Example 3 in view of their effect. Accordingly, it is considered that ursodesoxycholic acid and/or chenodesoxycholic acid have no significant effect on the plaque formation. Additionally, it is identified that ursodesoxycholic acid and/or chenodesoxycholic acid in combination with the extract of other medicinal herbs do not show any synergistic and antagonistic effect.

Meanwhile, as can be identified from the above Table 8, as the result of the siginificance examination in the gingivitis index measured after using the dentifrices of Examples 1 to 6 and Comparative Examples 1 to 4 for 4 weeks, it has been identified that the use of the compositions of Examples 1 to 6 and Compartive Examples 2 to 3 provides a siginificant effect of alleviating gingivitis in comparison with before use of the composition and that the composition of Exmple 6 shows a better gingivitis alleviating effect than the composition of Comparative Example 3. In addition, it has been identified that ursodesoxycholic acid begins to shows the effect of alleviating gingivitis at the concentration of 0.01 wt %, exhibits a significant effect at the concentration of 0.02 wt % or more in comparison with the composition of Comparative Example 4 not containing ursodesoxycholic acid, and at the concentration in excess of 1.0 wt % (Comparative Example 2) does not show any increase of the effect in proportion to the increase of the concentration. Accordingly, it is considered that ursodesoxycholic acid and/or chenodesoxycholic acid have a good effect of alleviating gingivitis. For this purpose, it is identified that ursodesoxycholic acid and/or chenodesoxycholic acid can be used at the concentration of 0.02 to 1.00 wt %, preferably 0.02 to 0.6 wt %, and when they are used in combination with bamboo salt, the extract of medicinal herbs, etc., shows the synergistic alleviating effect on gingivitis.

Experiment 4

The effect of inhibiting plaque formation and gingivitis was tested using the oral rinse compositions of Examples 7 to 12 and Comparative Examples 5 to 8 described in Table 2 according to the same method as Experiment 3. The results are described in the following Tables 9 and 10.

TABLE 9

Plaque index score

| Test oral rinse composition | Initial index | Index after 2 weeks | Index after 4 weeks | Improvement index |
|---|---|---|---|---|
| Example 7 | 1.30 ± 0.25 | 1.12 ± 0.23 | 0.95 ± 0.24 | 0.35 ± 0.24 |
| Example 8 | 1.31 ± 0.21 | 1.08 ± 0.26 | 0.89 ± 0.20 | 0.42 ± 0.22 |
| Example 9 | 1.30 ± 0.19 | 1.07 ± 0.21 | 0.85 ± 0.28 | 0.45 ± 0.18 |
| Example 10 | 1.30 ± 0.22 | 1.05 ± 0.22 | 0.82 ± 0.30 | 0.48 ± 0.29 |
| Example 11 | 1.32 ± 0.25 | 1.10 ± 0.22 | 0.92 ± 0.26 | 0.40 ± 0.25 |
| Example 12 | 1.30 ± 0.16 | 0.95 ± 0.15 | 0.59 ± 0.10 | 0.71 ± 0.13 |
| Comp. Example 5 | 1.29 ± 0.28 | 1.13 ± 0.26 | 0.99 ± 0.22 | 0.30 ± 0.22 |
| Comp. Example 6 | 1.32 ± 0.11 | 1.19 ± 0.12 | 0.84 ± 0.12 | 0.48 ± 0.12 |
| Comp. Example 7 | 1.31 ± 0.21 | 1.00 ± 0.19 | 0.73 ± 0.18 | 0.58 ± 0.13 |
| Comp. Example 8 | 1.33 ± 0.27 | 1.25 ± 0.22 | 1.17 ± 0.21 | 0.16 ± 0.20 |

TABLE 10

Gingivitis index score

| Test oral rinse composition | Initial index | Index after 2 weeks | Index after 4 weeks | Improvement index |
|---|---|---|---|---|
| Example 7 | 1.05 ± 0.32 | 0.87 ± 0.25 | 0.72 ± 0.22 | 0.33 ± 0.23 |
| Example 8 | 1.13 ± 0.28 | 0.91 ± 0.23 | 0.69 ± 0.20 | 0.44 ± 0.19 |
| Example 9 | 1.10 ± 0.20 | 0.82 ± 0.16 | 0.50 ± 0.28 | 0.60 ± 0.23 |
| Example 10 | 1.02 ± 0.23 | 0.76 ± 0.16 | 0.37 ± 0.12 | 0.65 ± 0.18 |
| Example 11 | 1.24 ± 0.26 | 0.96 ± 0.22 | 0.79 ± 0.29 | 0.45 ± 0.23 |
| Example 12 | 1.19 ± 0.18 | 0.65 ± 0.15 | 0.41 ± 0.10 | 0.78 ± 0.19 |
| Comp. Example 5 | 1.20 ± 0.21 | 1.11 ± 0.19 | 0.99 ± 0.15 | 0.21 ± 0.23 |
| Comp. Example 6 | 1.02 ± 0.31 | 0.63 ± 0.31 | 0.34 ± 0.19 | 0.68 ± 0.22 |
| Comp. Example 7 | 1.00 ± 0.27 | 0.74 ± 0.19 | 0.37 ± 0.14 | 0.63 ± 0.23 |
| Comp. Example 8 | 1.10 ± 0.21 | 1.05 ± 0.22 | 0.99 ± 0.38 | 0.11 ± 0.31 |

As can be seen from the above Tables 9 and 10, as the result of the siginificance examination in the plaque index and the gingivitis index measured after using the oral rinse compositions of Examples 7 to 12 and Comparative Examples 5 to 8 for 4 weeks, the same result as in the case of the dentifrice composition is obtained. Accordingly, it is also considered that in the oral rinse composition ursodesoxycholic acid and/or chenodesoxycholic acid have no significant effect on the plaque formation but show a good alleviating effect for gingivitis. For this purpose, ursodesoxycholic acid and/or chenodesoxycholic acid can be used at the concentration of 0.02 to 1.00 wt %, preferably 0.02 to 0.6 wt %. In addition, it is identified that when ursodesoxycholic acid and/or chenodesoxycholic acid are used in combination with bamboo salt, the extract of medicinal herbs, etc., they show the synergistic allevia- ting effect on gingivitis.

Experiment 5

The effect of inhibiting plaque formation and gingivitis was tested using the dentifrice compositions of Examples 13 to 19 and Comparative Examples 9 to 11 described in Table 3 according to the same method as Experiment 3. The results are described in the following Tables 11 and 12.

TABLE 11

Plaque index score

| Test dentifrice | Initial index | Index after 2 weeks | Index after 4 weeks | Improvement index |
|---|---|---|---|---|
| Example 13 | 1.72 ± 0.22 | 1.55 ± 0.27 | 1.39 ± 0.24 | 0.33 ± 0.28 |
| Example 14 | 1.73 ± 0.19 | 1.47 ± 0.15 | 1.26 ± 0.20 | 0.47 ± 0.17 |
| Example 15 | 1.72 ± 0.19 | 1.40 ± 0.18 | 1.21 ± 0.18 | 0.51 ± 0.28 |
| Example 16 | 1.72 ± 0.26 | 1.35 ± 0.25 | 1.11 ± 0.20 | 0.61 ± 0.29 |
| Example 17 | 1.73 ± 0.15 | 1.21 ± 0.12 | 0.91 ± 0.11 | 0.82 ± 0.14 |
| Example 18 | 1.74 ± 0.26 | 1.50 ± 0.19 | 1.30 ± 0.15 | 0.44 ± 0.13 |
| Example 19 | 1.72 ± 0.18 | 1.18 ± 0.16 | 0.85 ± 0.15 | 0.87 ± 0.15 |
| Comp. Example 9 | 1.72 ± 0.18 | 1.60 ± 0.17 | 1.51 ± 0.17 | 0.21 ± 0.22 |
| Comp. Example 10 | 1.73 ± 0.26 | 1.30 ± 0.19 | 1.09 ± 0.19 | 0.64 ± 0.13 |
| Comp. Example 11 | 1.74 ± 0.22 | 1.18 ± 0.12 | 0.85 ± 0.21 | 0.89 ± 0.15 |

TABLE 12

Gingivitis index score

| Test dentifrice | Initial index | Index after 2 weeks | Index after 4 weeks | Improvement index |
|---|---|---|---|---|
| Example 13 | 1.32 ± 0.22 | 1.13 ± 0.28 | 0.95 ± 0.25 | 0.37 ± 0.24 |
| Example 14 | 1.32 ± 0.24 | 1.02 ± 0.25 | 0.79 ± 0.24 | 0.53 ± 0.17 |
| Example 15 | 1.33 ± 0.30 | 0.96 ± 0.29 | 0.70 ± 0.18 | 0.63 ± 0.19 |
| Example 16 | 1.31 ± 0.25 | 0.95 ± 0.26 | 0.62 ± 0.22 | 0.69 ± 0.17 |
| Example 17 | 1.32 ± 0.25 | 0.96 ± 0.30 | 0.52 ± 0.25 | 0.80 ± 0.21 |
| Example 18 | 1.31 ± 0.24 | 1.00 ± 0.26 | 0.81 ± 0.23 | 0.50 ± 0.19 |
| Example 19 | 1.33 ± 0.21 | 0.86 ± 0.19 | 0.47 ± 0.25 | 0.86 ± 0.22 |
| Comp. Example 9 | 1.31 ± 0.33 | 1.23 ± 0.21 | 1.14 ± 0.28 | 0.19 ± 0.23 |
| Comp. Example 10 | 1.31 ± 0.28 | 0.99 ± 0.29 | 0.67 ± 0.23 | 0.64 ± 0.21 |
| Comp. Example 11 | 1.31 ± 0.30 | 0.86 ± 0.25 | 0.43 ± 0.28 | 0.88 ± 0.22 |

As can be seen from the above Table 11, as the result of the siginificance examination in the plaque index measured after using the dentifrices of Examples 13 to 19 and Comparative Examples 9 to 11 for 4 weeks, it has been identified that the use of the compositions of Examples 13 to 19 and Compartive Examples 9 to 11 provides a siginificant inhibiting effect on plaque formation in comparison with before use of the composition. In addition, the dentifrice containing the mixture of 0.01 to 1.00 wt % of ursodesoxycholic acid and/or chenodesoxycholic acid and 0.0001 to 1.000 wt % of triclosan shows a better effect for inhibiting plaque formation. Particularly, as can be seen from Example 17 and Comparative Example 10, the dentifrice containing the mixture of triclosan and ursodesoxycholic acid in a certain ratio shows a sperior effect of inhibiting plaque formation in comparison with the dentifrice containing triclosan only.

Meanwhile, as can be identified from the above Table 12 describing the result of the siginificance examination in the gingivitis index measured after using the dentifrices of Examples 13 to 19 and Comparative Examples 9 to 11 for 4 weeks, it has been identified that the use of the compositions of Examples 13 to 19 and Compartive Examples 10 to 11 provides a siginificant effect of alleviating gingivitis in comparison with before use of the composition. In addition, the dentifrice containing the mixture of 0.01 to 1.00 wt % of ursodesoxycholic acid and/or chenodesoxycholic acid and 0.0001 to 1.000 wt % of triclosan shows a better effect for alleviating and treating gingivitis. Particularly, as can be seen from Example 17 and Comparative Example 10, the dentifrice containing the mixture of triclosan and ursodesoxycholic acid in a certain ratio shows a sperior alleviating effect for gingivitis in comarison with the dentifrice containing triclosan only.

It has been identified that ursodesoxycholic acid and chenodesoxycholic acid as the effective component used in the present invention has a good activity for inactivating collagenase which is the inducer of gingivitis. Therefore, when these components are contained in dentifrice, oral rinse, chewing gum, oral massage cream, etc., these compositions can show a superior alleviating effect on gingivitis. In addition, by additionally including triclosan as the known bactericidal agent to the composition, the composition can provide a superior inhibiting effect on plaque formation as well as an increased gingivitis alleviating effect.

Furthermore, since the composition for enhancing oral hygiene having a good effect, as mentioned above, according to the present invention does not contain fel tauri and fel ursi as the crude drug originated from medicinal animals, it has some advantages that since it is substantially not possible to deteriorate the raw materials during the storage period, the stability during storage is good, the safety to human subject is high and thus the composition of the present invention can be conveniently used.

What is claimed is:

1. A composition for enhancing oral hygiene which comprises an effective amount of a compound selected from the group consisting of ursodesoxycholic acid and chenodesoxycholic acid; and an acceptable carrier for an oral rinse, a dentifrice, a chewing gum, an oral massage cream or an oral massage ointment.

2. A composition for enhancing oral hygiene which comprises an effective amount of ursodesoxycholic acid and an acceptable carrier for an oral rinse, a dentifrice, a chewing gum, an oral massage cream or an oral massage ointment.

3. A method of enhancing oral hygiene comprising administering to a person in need thereof an effective amount of the composition of claim 1.

4. A method of enhancing oral hygiene comprising administering to a person in need thereof an effective amount of the composition of claim 2.

5. The composition as defined in claim 1, wherein one or more component selected from the group consisting of ursodesoxycholic acid and chenodesoxycholic acid is contained in the ratio of 0.02 to 1.0 wt % with respect to the total weight of the composition.

6. The composition as defined in claim 2, wherein one or more component selected from the group consisting of ursodesoxycholic acid and chenodesoxycholic acid is contained in the ratio of 0.02 to 0.6 wt % with respect to the total weight of the composition.

7. The composition as defined in claim 1, wherein the effective component is the mixture of ursodesoxycholic acid and chenodesoxycholic acid in the mixing ratio of 100:1 to 1:100 on the basis of weight.

8. The composition as defined in claim 1, which further contains triclosan.

9. The composition as defined in claim 8, wherein it contains 0.01 to 1.0 wt % of one or more component selected from the group consisting of ursodesoxycholic acid and chenodesoxycholic acid and 0.0001 to 1.0 wt % of triclosan, with respect to the total weight of the composition.

10. The composition as defined in claim 9, wherein it contains 0.02 to 0.6 wt % of one or more component selected from the group consisting of ursodesoxycholic acid and chenodesoxycholic acid and 0.001 to 0.300 wt % of triclosan, with respect to the total weight of the composition.

11. The composition as defined in claim 1, which further contains one or more substance selected from the group consisting of sodium fluoride, sodium fluorophosphate, fluoroamine, tin fluoride, chlorhexidine, bamboo salt, tranexamic acid, allantoins, caproic acids, enzymes, and extracts of *Phellodendri cortex, Platycodi radix, Schizonepetae herba, Gardeniae fructus, Glycyrrhizae radix* and *Sanguinaria radix* as the adjuvant effective component.

12. The composition as defined in claim 11, wherein it contains 1.0 to 5.0 wt % of bamboo salt, 0.01 to 5.0 wt % of the extracts of *Phellodendri cortex, Platycodi radix* and *Schizonepetae herba* as the total weight and 0.1 to 1.0 wt % of fluoride compound, with respect to the total weight of the composition.

13. The composition as defined in claim 1, which is a dentifrice.

14. The composition as defined in claim 1, which is a oral rinse.

15. The composition as defined in claim 1, which is a chewing gum.

16. The composition as defined in claim 1, which is a oral massage cream.

* * * * *